United States Patent [19]

Israel et al.

[11] Patent Number: 5,200,405
[45] Date of Patent: Apr. 6, 1993

[54] USE OF N-(1-HEXAHYDROAZEPINYLALKYL) ACETAMIDES FOR THE TREATMENT OF CHOLINERGIC TRANSMISSION DISORDERS

[75] Inventors: Maurice Israel, Bures sur Yvette; Yvette Morot-Gaudry, Gif sur Yvette; Max Robba, Paris; Gérard Adam, Le Mesnil le Roi; Pierre Renard, Versailles, all of France

[73] Assignee: Adir et Compagnie, Courbevoie, France

[21] Appl. No.: 758,905

[22] Filed: Sep. 11, 1991

[30] Foreign Application Priority Data

Sep. 12, 1990 [FR] France .................. 90 11266

[51] Int. Cl.$^5$ .............................. A61K 31/55
[52] U.S. Cl. ............................ 514/212; 514/879
[58] Field of Search ................. 514/212, 879

[56] References Cited

PUBLICATIONS

CA 80:3401u, Robba et al., 1973.
Corkin, Trends in Neuro Science—TINS, Dec. 1981, pp. 287–290; "Acetyl choline aging and alzheimer's disease—implications for treatment".
Goodman, et al., Goodman & Gillman's "The pharmacological basis of therapeutics", 8th Edition, pp. 131, 145, 146, 147, 1544 (1990).

Primary Examiner—Frederick E. Waddell
Assistant Examiner—Kimberly Jordan
Attorney, Agent, or Firm—Gordon W. Hueschen

[57] ABSTRACT

The invention relates to the use of a compound selected from those of formula (I):

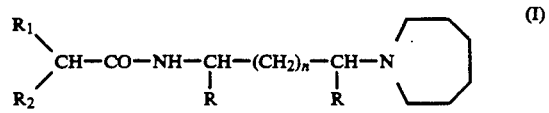

in which R, $R_1$, $R_2$ and n are as defined in the description, for the treatment of cholinergic transmission disorders.

7 Claims, No Drawings

USE OF N-(1-HEXAHYDROAZEPINYLALKYL) ACETAMIDES FOR THE TREATMENT OF CHOLINERGIC TRANSMISSION DISORDERS

The present invention relates to the use of N-(1hexahydroazepinylalkyl)acetamides for the treatment of cholinergic transmission disorders.

N-(1-hexahydroazepinylalkyl)acetamides having spasmolytic or vasodilator properties are known from the prior art, especially German Patent DE 2313338.

The Applicant has now discovered that such N-(1hexahydroazepinylalkyl)acetamides possess the surprising property of influencing cholinergic transmission by powerful stimulation of the release of acetylcholine.

The consequence of this activity is an increase in the concentration of acetylcholine in the cholinergic synapse and the neuromuscular junction, permitting application in pathologies resulting from a central or peripheral cholinergic deficiency, such as Alzheimer's disease, certain intellectual deficiencies as a result of senescence, or myasthenia.

Indeed, a change in nerve impulse transmission in the cholinergic synapses of the central nervous system constitutes one of the physiological causes of the symptomatology associated with Alzheimer's disease (Johns C.A. et al. "The cholinergic treatment strategy in aging and senile dementia". Psychopharmacol. Bull—1983, 19, 185–187; Collerton D "Cholinergic function and intellectual decline in Alzheimer's disease". Neuroscience 1986, 19, 1–28) and intellectual and cognitive disorders associated with senescence (Davidson M et al. "Cholinergic mechanisms in the treatment of geriatric disorders" Psychopharmacol—Bull, 1986, 22, 101–105).

Some of the treatments currently proposed for Alzheimer's disease are moreover based on stimulation of the cholinergic system,
- either directly as in the administration of parasympathomimetic (arecoline) agents,
- or indirectly by precursors of acetylcholine (choline, lecithin) which increase the production of acetylcholine in the synaptic region, or by acetylcholinesterase (physostigmine) inhibitors which reduce the enzymatic degradation of the neurotransmitter.

These therapeutic agents, however, have disadvantages associated with the short half-life of the active ingredient and with a feedback that reduces the production of acetylcholine in the neurone.

Myasthenia is characterised by a post-synaptic block of the neuromuscular junction, the contact zone between the motorneurons and the effector muscle (Engel A.G. et al. "Histometric analysis of the ultrastructure of the neuromuscular junction in myasthenia gravis and the myasthenic syndrome". Ann. N.Y. Acad. Sci., 1976, 1 183, 46–63). The neurotransmitter responsible for the transmission of the nerve impulse at the neuromuscular junction is acetylcholine. While myasthenia is probably of auto-immune origin, it is expressed physiologically in a block of cholinergic transmission and the only medicaments that have exhibited any activity in treating this disease are acetylcholinesterase inhibitors, but their use is limited by the frequency of the side effects they cause.

Compounds like the ones used according to the invention that stimulate the release of physiological acetylcholine therefore have a natural application particularly in the treatment of Alzheimer's disease and related disorders, myasthenia, and any other central or peripheral complaints resulting from a deficiency in cholinergic transmission, and a stimulation of natural release would not be expected to cause any side effects.

More specifically, the invention relates to the use for the treatment of cholinergic transmission disorders, of a compound selected from those of formula I

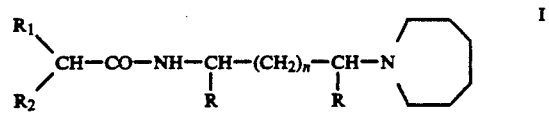

in which:
R represents a radical selected from hydrogen and alkyl containing from 1 to 4 carbon atoms,
n represents 0, 1, 2, 3 or 4,
$R_1$ and $R_2$, which may be the same or different, represent a radical selected from :
straight-chain or branched alkyl or alkenyl containing from 1 to 6 carbon atoms,
cycloalkyl containing from 3 to 7 carbon atoms or cycloalkenyl containing from 5 to 7 carbon atoms,
and aryl, aralkyl, heteroaryl or heteroaralkyl optionally substituted by one or more groups selected from halogen, alkoxy, nitro, trifluoromethyl, and hydroxyalkyl,
of its isomers thereof and also of its addition salts thereof with a pharmaceutically-acceptable acid.

Aryl denotes phenyl or naphthyl radicals and heteroaryl denotes furyl, thienyl, pyrrolyl, imidazolyl, benzofuryl, benzothienyl, benzimidazolyl or indolyl radicals.

As pharmaceutically acceptable acids that can be used to convert compounds of formula I into salts, there may be mentioned by way of non-limiting examples hydrochloric, hydrobromic, sulphuric, nitric, oxalic, fumaric, tartaric, methanesulphonic, ethanesulphonic, camphoric, camphorsulphonic, citric, malic and maleic acid etc..

The invention extends to the use of pharmaceutical compositions in the treatment of Alzheimer's disease, of cerebral disorders associated with senescence, or of myasthenias, comprising as active ingredient a compound of formula I, an isomer thereof, or an addition salt thereof with a pharmaceutically acceptable acid, in association with one or more inert non-toxic excipients.

The medicaments obtained by using, in accordance with the invention, a compound of formula I, an isomer thereof or a pharmaceutically acceptable salt thereof, are advantageously presented in various forms, such as, for example, tablets, dragees, gelatin capsules, glossettes or other galenic preparations suitable for sublingual administration, suppositories, solutions for endobuccal pulverisation, galenic preparations suitable for percutaneous administration, and injectable or drinkable solutions.

The posology can vary widely depending on the age of the patient, his weight, the route and the frequency of administration, the seriousness of the complaint from which the patient is suffering and associated treatments, and ranges from 0.05 to 150 mg per dose or administration.

The invention is illustrated, in a non-limiting manner, by the activity on cholinergic transmission of the following compounds:
compound A : the hydrochloride of N-[3-(1-hexahydroazepinyl)-propyl]-diphenylacetamide compound B : the hydrochloride of N-[2-(1-hexahydroazepinyl)-ethyl]-diphenylacetamide compound C : the hydrochloride of cyclohexyl N-[3-(1-hexahydroazepinyl)-propyl]-thien-3-ylacetamide, compound D : the hydrochloride of cyclohexyl N-[3-(1-hexahydroazepinyl)-propyl]-benzo[b]thien-2-ylacetamide.

The tests reported are carried out on the electric organ of the torpedo (Torpedo marmorata), which is known to be embryologically homologous with the cholinergic neuromuscular junctions of higher vertebrates.

EXAMPLE 1

Stimulation of the Release of Acetylcholine

The cholinergic nerve endings of the electric organ of a torpedo are isolated according to the method described by M. ISRAEL (Biochem. J. 1976, 160, 113–115). The synaptosomes are purified on a discontinuous density gradient using isoosmotic sucrose/NaCl mixtures approximating to torpedo serum, composed of 250 mM NaCl, 3 mM KCl, 1.8 mM $MgCl_2$, 3.4 mM $CaCl_2$, 5 mM $NaHCO_3$, 5.5 mM glucose, 300 mM urea and 100 mM sucrose. The pH is adjusted to a value of 7.1 with 1.2 mM sodium phosphate buffer, after equilibration with $O_2$.

The endings prepared in this manner are capable of synthesising radioactive acetylcholine from labelled precursors (choline and acetate); they are rich in acetylcholine which they are capable of releasing when stimulated.

The release of acetylcholine is triggered, in the presence of 3.5 mM calcium, by the addition of a calcium ionophore, A23187 at a concentration of 3.5 μM, which penetrates the synaptosomal membrane and permits, by electroneutral exchange between the extracellular calcium and the intracellular cations, an increase in the cytoplasmic calcium concentration and the release of the neurotransmitter.

In practice, 50 μl volumes of the synaptosomal preparation, corresponding to 30 mg of tissue, are diluted in 450 μl of an alkaline solution approximating to torpedo serum (see above). The administration of the test compounds in this medium takes place for 3 to 5 minutes before the release of acetylcholine is triggered.

The amount of acetylcholine is determined by the chemiluminescence method described by ISRAEL and LESBATS (J. Neurochem, 1981, 37, 1475 and Neurochem Int, 1981, 3, 81). The emission of light, which occurs for several minutes, is calibrated immediately after by comparison with an internal standard of acetylcholine. At the end of the release experiment, the addition of Triton X-100 (0.05 %) causes rupture of the synaptosomal membranes, thus allowing the acetylcholine still occluded in the synaptosomes of the sample to be determined.

The compounds used in accordance with the invention exhibit the property of stimulating the release of acetylcholine when that release is induced by an increase in intracellular calcium by the addition of the calcium ionophore A 23187 in the presence of calcium, as shown in the following Table:

| PERCENTAGE RELEASE OF ACETYLCHOLINE INDUCED BY THE COMPOUNDS OF THE INVENTION | | | | | |
|---|---|---|---|---|---|
| | Concentration (μM) | | | | |
| Compounds | 0 | 4,9 | 19,6 | 49 | 98 |
| A | 100 | 102 | 130 | 104 | 123 |
| B | 100 | ND* | 91 | 116 | 118 |
| C | 100 | 111 | 138 | 136 | 125 |

*ND: not determined

EXAMPLE 2

Injectable Solution Containing 0.1 mg/ml of the Hydrochloride of Cyclohexyl N-[3-(1-Hexahydroazepinyl)-propyl]-thien-3-ylacetamide

| | |
|---|---|
| hydrochloride of cyclohexyl N-[3-(1-hexahydroazepinyl)-propyl]-thien-3-yl-acetamide | 0.2 g |
| water for injectable preparation, ad | 2 l |

(quantities for 1000 injectable ampoules each containing 0.02 mg of active ingredient).

EXAMPLE 3

Gelatin Capsules each Containing 1 mg of the Hydrochloride of Cyclohexyl N-[3-(1-Hexahydroazepinyl)-propyl]-benzo[b]thien-2-ylacetamide

| | |
|---|---|
| hydrochloride of cyclohexyl N-[3-(1-hexahydroazepinyl)-propyl]-benzo[b]thien-2-ylacetamide | 1 g |
| magnesium stearate | 5 g |
| lactose | 20 g |
| colloidal silica | 1 g |

(quantities for 1000 size 2 gelatin capsules each containing 1 mg of active ingredient)

We claim:

1. A method, using as active principle a compound selected from those of formula I :

$$R_1\!\!\diagdown\!\!\!\!\phantom{X}\atop R_2\!\!\diagup\!\!\!\!\phantom{X}CH-CO-NH-\underset{R}{CH}-(CH_2)_n-\underset{R}{CH}-N\!\!\diagup\!\!\!\!\!\diagdown$$  (I)

in which:

R represents a radical selected from : hydrogen and alkyl containing 1 to 4 carbon atoms inclusive, n represents 0, 1, 2, 3 or 4, $R_1$ and $R_2$, which may be the same or different, represent a radical selected from :

straight-chain or branched alkyl or alkenyl containing 1 to 6 carbon atoms inclusive, cycloalkyl containing 3 to 7 carbon atoms inclusive, or cycloalkenyl containing 5 to 7 carbon atoms inclusive, aryl, aralkyl, heteroaryl or heteroaralkyl optionally substituted by one or more groups selected from halogen, alkoxy, nitro, trifluoromethyl, and hydroxyalkyl, aryl designating phenyl or naphthyl, and heteroaryl designating furyl, thienyl, pyrrolyl, o imidazolyl, benzofuryl, benzothienyl, benzimidazolyl or indolyl, an isomer thereof, or an addition salt thereof with a pharmaceutically-acceptable acid, of stimulating acetyl choline release in a living animal afflicted with Alzheimer's Disease of a myasthenia, comprising the step of administering to the said living animal an amount of a compound of formula I which is effective for alleviation of the said condition.

2. A method of treating, according to claim 1, using a compound selected from N-[3-(1-hexahydro-azepinyl)-propyl]diphenylacetamide, an isomer thereof, and an addition salt thereof with a pharmaceutically-acceptable acid.

3. A method of treating, according to claim 1, using a compound selected from N-[2-(1-hexahydro-azepinyl)-ethyl]diphenylacetamide, an isomer thereof, and an addition salt thereof with a pharmaceutically-acceptable acid.

4. A method of treating, according to claim 1, using a compound selected from cyclohexyl N-[3-(1-hexahydroazepinyl)propyl]-thien-3-ylacetamide, an isomer thereof, and an addition salt thereof with a pharmaceutically-acceptable acid.

5. A method of treating, according to claim 1, using a compound selected from cyclohexyl N-[3-(1-hexahydroazepinyl)propyl]-benzo[b]thien-2-ylacetamide, an isomer thereof, and an addition salt thereof with a pharmaceutically-acceptable acid.

6. A method of treating, according to claim 1, using a pharmaceutical composition containing as active principle a compound of formula 1 in combination with a pharmaceutically-acceptable excipient or vehicule.

7. A method of treating, according to claim 1, wherein the active principle is administered in a range from 0,5 mg to 150 mg per dose.

* * * * *

UNITED STATES PATENT AND TRADEMARK OFFICE
CERTIFICATE OF CORRECTION

PATENT NO. : 5,200,405
DATED : Apr. 6, 1993
INVENTOR(S) : Maurice Israel, Yvette Morot-Gaudry, Max Robba, Gérard Adam, Pierre Renard It is certified that error appears in the above-indentified patent and that said Letters Patent is hereby corrected as shown below:

Column 1, line 6; "N-(1hex-" should read -- N-(1-hex- --.
Column 1, line 55; "1 183," should read -- 183, --.
Column 3, line 17; insert "In Vitro" after "Acetylcholine".
Column 4, approximately line 25; "0.02" should read --0.2--.
Column 4, approximately line 30; "-propyl)-" should read
     -- -propyl]- --.
Column 4, line 60; "atoms inclusive," should read
     -- atoms, inclusive, --.
Column 4, line 63; "atoms inclusive" should read
     -- atoms, inclusive, --.
Column 5, line 1; "lyl, o imidazolyl," should read
     -- lyl, imidazolyl, --.
Column 5, line 7; the first "of" should read -- or -- .
     (R&A 9-11-92)
Column 6, line 16; "vehicule." should read --vehicle--.
Column 6, line 19; "0,5" should read -- 0.5 --.

Signed and Sealed this

Twenty-second Day of March, 1994

Attest:

BRUCE LEHMAN

Attesting Officer

Commissioner of Patents and Trademarks